United States Patent
Merkle et al.

(10) Patent No.: US 6,217,926 B1
(45) Date of Patent: Apr. 17, 2001

(54) AQUEOUS EXTRACTION PROCESS TO SELECTIVELY REMOVE PHOSPHOLIPID FROM EGG YOLKS

(75) Inventors: Jonathan A. Merkle, Green Isle; Herschell Ball, Waconia, both of MN (US)

(73) Assignee: Michael Foods, Inc., Minneapolis, MN (US)

(*) Notice: Subject to any disclaimer, the term of this patent is extended or adjusted under 35 U.S.C. 154(b) by 0 days.

(21) Appl. No.: 09/342,759

(22) Filed: Jun. 29, 1999

Related U.S. Application Data (60) Provisional application No. 60/091,322, filed on Jun. 30, 1998.

(51) Int. Cl.[7] .................................................. A23L 1/32
(52) U.S. Cl. .................... 426/425; 426/614; 426/431; 426/490
(58) Field of Search .................. 426/614, 425, 426/431, 490

(56) References Cited

U.S. PATENT DOCUMENTS

| | | |
|---|---|---|
| 3,958,034 | 5/1976 | Nath et al. |
| 4,157,404 | 6/1979 | Yano et al. |
| 4,219,585 | 8/1980 | Herring |
| 4,670,285 | 6/1987 | Clandinin et al. |
| 4,844,926 | 7/1989 | Hatanaka |
| 4,847,015 | 7/1989 | Shigematsu et al. |
| 5,069,903 | * 12/1991 | Stitt |
| 5,302,405 | 4/1994 | Hsieh et al. ................. 426/271 |
| 5,656,319 | 8/1997 | Barclay |

OTHER PUBLICATIONS

Kim I. J. et al, "Establishment of aqueous extraction condition for the separation fo cholesterol from egg yolk using response surface method" XP002122817; vol. 38, No. 3, 1996 pp. 299–306.

Kim I. J. et al. "Aqueous Extracton of cholesterol From Egg Yolks", XP002122818; vol. 38, No. 5, 1996 pp. 519–526.

Zhi–Bin Huange et al: "Effect of Dietary Fish Oil on W–3 Fatty Acids Levels in Chicken Eggs and Thigh Flesh",; XP000102235; *Journal of Agricultural and Food Chemistry, US, American Chemical Society*, col. 38, No. 3, p. 743–747.

Database WPI, XP002122819; Derwent Publications, Ltd., London, GB: 1995–348501.

Database WPI, XP002122820; Derwent Publications, Ltd., London, GB; 1979.

(List continued on next page.)

*Primary Examiner*—Anthony J. Weier
(74) *Attorney, Agent, or Firm*—Vidas, Arrett & Steinkraus, P.A.

(57) ABSTRACT

The Aqueous Extraction Process To Selectively Remove Phospholipid From Egg Yolks in general utilizes an aqueous method to separate a majority of the proteins from the egg yolk material using ionic strength, pH and gravitational centrifuge forces. The method is initiated by the separation of the egg yolks from the albumen. Next the egg yolk material is mixed with water to dilute the egg yolk into a DY fraction. The pH of the mixed egg yolk material is then adjusted by the addition of acids, bases, and/or salts. The adjusted and mixed egg yolk material is then exposed to gravitational separation through the use of a centrifuge into layers of a DYS fraction and a DYP fraction. The DYS fraction is then separated from the DYP fraction. Viscosity agents are then added to the DYS fraction where blending occurs. The DYS fraction is exposed to gravitational separation forces for separation into a cream CMC P fraction and an aqueous fraction. The cream CMC P fraction is then separated from the aqueous fraction to provide the desired phospholipid separation. The method may also utilize a feeding regime of extruded whole soy beans and flax seed to egg laying hens to increase the concentration of omega-3 fatty acid (docosahexaenoic acid) within the starting egg yolk material.

20 Claims, 4 Drawing Sheets

OTHER PUBLICATIONS

Barbara Tokarska and Michael T. Clandinin, Extraction of Egg Yolk of Reduced Cholesterol Content, *Can. Inst. Food Sci. Technol. J.*, vol. 18, No. 3, pp. 256–258, 1985.

L. Kwan, E. Li–Chan, N. Helbig, and S. Nakai, Fractionation of Water–Soluble and –Insoluble Components from Egg Yolk with Minimum Use of Organic Solvents, *Journal of Food Science*, vol. 56, No .6, pp 1537–1541, 1991.

Abstracts for the following US patents: 4,219,585; 5,314,706; 5,466,842; 5,089,268; 5,464,639; 4,670,285.

F. DeMeester, New Developments in Yolk–Containing Egg Powders, *Food Ingredients Europe*, London, Oct. 1994, Process Press Europe, pp. 236,240.

G.W. Froning et al., Extracting of Cholesterol and Other Lipids from Dried Egg Yolk Using Supercritical Carbon Dioxide, *Journal of Food Science*, vol. 55, No. 1, 1990, pp. 95–98.

A. Paraskevopoulou and V. Kiosseoglou, Cholesterol and Other Lipid Extraction from Egg Yolk Using Organic Solvents; Effects on Functional Properties of Yolk, *Journal of Food Science*, vol. 59, No .4, 1994, pp. 766–768.

Ladislov Kolaroiv and Nestor C. Fournier, A Comparison of Extraction Methods for the Isolation of Phospholipids from Biological Sources, *Analytical Biochemistry*, 156, 1986, pp. 244–250.

Abalo C. Awade, On hen egg fractionation: applications of liquid chromatography to the isolation and the purification of hen egg white and egg yolk proteins, *Z Lebnsm Unters Forsch*, 1996, 202, pp. 1–14.

E.M. Akita and S. Nakai, Immunoglobulins from Egg Yolk: Isolation and Purification, *Journal of Food Science*, vol. 57, No. 3,1992, pp. 629–634.

A. Paraskevopoulou and V. Kiosseoglou, Texture Profile Analysis of Heat–Formed Gels and Cakes Prepared with Low Cholesterol Egg Yolk Concentrates, *Journal of Food Science*, vol. 62, No .1, 1997, pp. 208–211.

Hideaki Yokoyama et al., A Two–Step Procedure of Purification of Hen Egg Yolk Immunoglobulin G: Utilization of Hydroxypropylmethylcelluose Phthalate and Synthetic Affinity Ligand Gel (Avid AL®), *Poultry Science*, 1993, 72, pp. 275–281.

Basant B. Shah and Rakesh K. Singh, Separation of Egg Yolk Proteins and Lipids With Carboxymethyl Cellulose, *Journal of Food Processing and Preservation 16*, 1992, pp. 275–288.

Makoto Shimizu et al., Egg Yolk Antibody (IgY) Stability in Aqueous Solution with High Sugar Concentrations, *Journal of Food Science*, vol. 59, No. 4, 1994, pp. 763–772.

H. Hatta et al., Separation of Phospholipids from Egg Yolk and Recovery of Water–Soluble Proteins, *Journal of Food Science* vol. 53, No. 2, 1988, pp. 425–431.

J. Fichtali et al., Purifications of Antibodies from Industrially Separated Egg Yolk, *Journal of Food Science*, vol .58, No. 6, 1993, pp. 1282–1285 and 1290.

* cited by examiner

Fig. 3. Dietary Effects on Egg Production

Fig. 4. Figure 2. Dietary Effects on Feed Consumption

AQUEOUS EXTRACTION PROCESS TO SELECTIVELY REMOVE PHOSPHOLIPID FROM EGG YOLKS

CROSS REFERENCE TO RELATED APPLICATION

This application is a continuation of co-pending U.S. Provisional Application Ser. No. 60/091,322, filed Jun. 30, 1998.

BACKGROUND

Proteins and lipids are the major constituents of egg yolk. Both fractions play important roles in the food processing, cosmetic, and pharmaceutical industry. The most plentiful constituent in egg yolk solids is the lipid fraction which constitutes approximately ⅓ of the raw yolk. The lipid is comprised mainly of various phospholipids containing mainly phosphatidylcholine or lecithin, then by cholesterol, a relatively minor constituent in the egg yolk. Proteins constitute 15% to 17% of the yolk, including phosvitin, $\alpha$- and $\beta$-lipovitellins and low density lipoproteins in the yolk granule and $\alpha$-$\beta$-, and $\gamma$-livetins as well as lipoproteins in the yolk plasma. $\gamma$-livetin has been recognized as the IgG-like antibody and is also commonly referred to a yolk immunoglobulin or IgY.

Due to the ready availability of egg yolk, many attempts have been made to isolate phospholipids (lecithin), IgY, and other bioactive or functional compounds. However, it is difficult to recover lipid components without denaturing or inactivating the egg yolk protein components.

Several methods for the extraction of phospholipids from egg yolk are known to those skilled in the art: the scorching method; solvent extraction of liquid egg yolk; and solvent extraction of dry egg yolk.

The scorching method comprises direct heating of egg yolk, either liquid or cooked, until the egg yolk proteins scorch. The yolk proteins are of no further value after this process. The extraction efficiency of this process is low because a large amount of egg lipids remain adhered to the protein residue. Furthermore, the extraction process results in deterioration of the unsaturated fatty acids because of the high temperature and exposure to the atmosphere. For these reasons, the scorching process has not been implemented on a commercial basis to extract egg phospholipids.

Solvent extraction of liquid egg yolk using a mixture of polar and non-polar solvents has been effectively applied to the extraction of egg lipids, which contain the desired egg yolk lecithin. Since the extraction process uses a mixture of solvents, the procedures for recovery are complicated and cannot be conducted economically. Further, solvents used may have boiling points sufficiently high to expose the egg lipid to temperatures in which oxidation of the valuable components occurs readily. During the heating process to remove the solvents, the egg yolk extract typically changes in color from yellow to orange to brown. The quality of the egg yolk lecithin obtained through this process may be extremely poor.

In the past the industry has practiced solvent extraction of lecithin from a yolk, by the use of dried yolk as a starting material, where the dried yolk was obtained by drying a raw yolk with heated air. The dried yolk was subjected to extraction with a solvent mixture of a polar solvent such as methanol or acetone in a non-polar solvent such as chloroform, diethyl ether or trichlorolethylene. Since this solvent mixture contains two different kinds of component solvents, the procedures for recovery of the component solvents during the extraction process are complicated and cannot be conducted economically. Further, solvents used may have boiling points in excess of 35° C. Therefore, for complete removal of the solvents from the extract, the extract may be required to be heated to high temperatures through use of steam or to be subjected to exposure of high temperatures for prolonged periods of time under reduced pressure. Yolk lecithin is extremely susceptible to oxidation. The yolk lecithin may be required to be heat-treated at a temperature as high as 60° C. or more under atmospheric pressure to remove residual solvent. During this heat treatment color of the yolk lecithin generally changes from yellow to orange to brown. The quality of the yolk lecithin obtained through the heat treatment for the removal of the solvents may be extremely poor, the yolk lecithin produced by such conventional solvent extraction methods also may smell bad and be colored brown. The conventional process for lecithin and lipid extraction utilizes organic solvents, whereby proteins are inevitably denatured. Typically, egg yolk is dried, usually by spray drying. The powder is extracted with a short chain alcohol, such as methanol or ethanol, or other suitable solvent(s) to yield a crude egg oil. This oil contains the desired phospholipids. The extraction process results in non-functional, denatured egg protein that can not be used for typical functional applications.

An alternative to conventional solvent extraction procedures for separating lecithin and cholesterol from egg oil is the use of supercritical fluid extraction, however, even under these conditions, some proteins are denatured.

Since egg yolk is a mixture of lipids, lipid proteins and water-soluble proteins, the water-soluble fraction including IgY may be extracted in undenatured form with water before further fractionation of the water soluble components. These procedures use a water dilution process with pH and salt adjustments. These processes are optimized to separate the IgY into the supernatant portion while directing the lipids, including phospholipids, into the pellet fraction. These processes typically utilize an acidic pH. The phospholipids may be further recovered from the pellet by resuspension and additional extraction. This additional work to recover the phospholipids is not practical on an industrial scale. Some attempts have also been made to separate the $\gamma$-livetins from egg yolk by using polyethylene glycol or sodium dextran sulfate.

Egg yolk lipids are suitable for food, cosmetic, and pharmeceutical application. Each of these applications may require a different composition of the lecithin fraction. In order to obtain these variations, it is necessary to selectively obtain egg which contain the desired egg yolk lecithin. One type application which may require a specific egg yolk lecithin composition is for the use in infant formula. Egg lipids may be a logical source of lipid to enable a product to be made that is analogous in fatty acid composition to the lipid constituents of human milk. Human milk contains a variety of chain elongated—unsaturated fatty acids derived from $C_{18:2}\omega6$ and $C_{18:30}\omega3$. These polyunsaturated homologs of the essential fatty acids are not found in presently available commercial formulas. A need therefore exists to prepare an oil which could provide these constituents for use in infant formula as derived from egg oil.

In general the yolk of various strains of chicken eggs is 30% to 36% lipid comprising about 65% triglycerides, 28.3% phospholipids and 5.2% cholesterol. The total amount of saturated fatty acid is approximately 40% of the fatty acids. Major unsaturated fatty acids are oleic, linoleic, and linolenic with a small quantity of $C_{20}\omega6$, $C_{22}\omega6$ and $C_{22}\omega 3$ polyunsaturated fatty acids. In recent years, efforts have been directed to produce a milk-based infant formula which is similar to human milk. In general, a dietary product is required which may be added to commercially available cow's milk. The dietary product is intended to adapt the cow's milk to the requirements of human nursing and to make the cow's milk similar to human milk. A lipid component of the dietary product is preferably a mixture of vegetable oil with soy lecithin and eventually with milk fats.

A problem with the past is that the oils used as the additive do not contain $C_{20}$ and $C_{22}$ omega-6 and omega-3 fatty acids which are present in human milk. Accordingly, these dietary preparations do not provide a balance of fatty acids that are similar in composition to that of human milk.

Studies have revealed that an adequate intake of mother's own milk could produce from 90 milligrams to 130 milligrams of $C_{20}$ and $C_{22}$ omega-6 fatty acids per day and 55–75 milligrams of $C_{20}$ and $C_{22}$ omega3 fatty acids per day. In view of these studies, dietary formulas for the premature/and pre-term infant should contain $C_{20}$ and $C_{22}$ omega-6 fatty acids and $C_{20}$ and $C_{22}$ omega-3 fatty acids to promote healthy growth. Fatty acids may have particular significance for the synthesis of structural lipids in brain tissue, however, these studies do not suggest any means for determining the quantities of these fatty acids required in infant formula. It may be advisable to provide essential fatty acids in a dietary formula for premature infants to insure normal synthesis of nerve tissues. It is particularly important that the quantifies of $C_{20}$ and $C_{22}$ omega-6 and omega-3 fatty acids be limited to appropriate ranges in the dietary formula, therefore, over feeding of these fatty acids should be avoided to minimize complications with prostaglandin metabolism and other adverse effects on an infant's physiology.

Omega-3 highly unsaturated fatty acids are of significant commercial interest in that they had been recently recognized as important dietary compounds for preventing arterialsclerosis and coronary heart disease, for alleviating inflammatory conditions and for retarding the growth of tumor cells. These beneficial effects are a result of both the omega-3 highly unsaturated fatty acids causing competitive inhibition of compounds produced from omega-6 fatty acids and from beneficial compounds produced directly from the omega-3 highly unsaturated fatty acids themselves. Omega-6 fatty acids are the predominant highly unsaturated fatty acids found in plants and animals. Currently the only commercially available dietary source of omega-3 highly unsaturated fatty acids is from certain fish oils which can contain up to 20% to 30% of these fatty acids. Beneficial effects of these fatty acids may be obtained by eating fish several times during a week or by daily intake of concentrated fish oil. Consequently, large quantities of fish oil are processed and capsulated each year for sale as a dietary supplement.

Several significant problems exist with these fish oil supplements. First, fish oil supplements may contain high levels of fat-soluble vitamins which are found naturally in fish oils. When ingested, these vitamins are stored and metabolized as fat in the human body rather than excreted. High doses of these vitamins may be unsafe, leading to kidney problems or blindness. Secondly, fish oils containing up to 80% of the saturated and omega-6 fatty acids both of which may have deleterious health affects. Additionally, fish oils have a strong fishy taste and odor and as such cannot be added to processed foods as a food additive without negatively effecting the taste of the food product. Moreover, the isolation of pure omega-3 highly unsaturated fatty acids is a relatively expensive process resulting in very high prices.

The present invention is directed to a method for separation of an egg yolk into desired fractions. The egg yolk contains many beneficial molecules which are valued for functional and biological characteristics following consumption. An unprocessed and uncooked egg yolk, in general, comprises water, yolk proteins and egg lipids. The egg yolk lipids comprises neutral lipids, yolk lecithin, sterols, and cholesterol. The conventionally proposed methods for removal of egg lipids from raw egg yolk are classified into two kinds of methods, namely the scorching method and a solvent extraction method.

In the past, the separation of an egg yolk into desired fractions, where each fraction had different functional and practical purposes, occurred through the method of utilizing solvents, or conditions which in turn caused the protein fractions of the egg yolk to denature. A method has not been previously known for separation of an egg yolk into desired fractions through processes utilizing mild food grade solvents which did not cause the resulting protein fractions to denature.

In the past, egg yolk phospholipids were separated from egg yolk by a tedious extraction process. In this extraction process, the egg yolk was first dried. The dried powder was then solvent extracted with a polar solvent such as ethanol, to remove the phospholipids. The solvent was then evaporated to yield phospholipids while the remainder of the egg yolk powder was no longer suitable as a functional food ingredient.

SUMMARY OF THE INVENTION

A principal object of the present invention is to separate an egg yolk into desired fractions for isolation of the phospholipids through a method of utilizing a mild food grade solvent which does not cause the resulting protein fractions to denature.

It is another principal object of the present invention to separate an egg yolk into desired fractions through utilization of a method of relatively simple and inexpensive design and operation which is safe and which fulfills the intended purpose of providing phospholipid and protein fractions which do not denature and where all components are of food grade quality to further maintain wholesomeness. (Subsequently, egg yolk shall refer to uncooked egg yolk or to egg yolk which has been pasteurized under such conditions that it may be separated using this process).

It is still another principal object of the present invention to utilize an aqueous method to separate a majority of proteins from the phospholipids from egg yolk material using ionic strength, pH and gravitational force.

It is still another object of the present invention to isolate through centrifuge separation techniques the phospholipids from the bulk of the proteins of the egg yolk material containing 70 to 100% of the original phospholipid starting material.

It is still another object of the present invention to provide a stable liquid infant formula with an improved fatty acid composition having suitable shelf life.

It is still another object of the present invention to provide an edible fat product for incorporation into a formula suitable for pre-term infants which will contain appropriate levels of C20 and C22 omega-6 and omega-3 fatty acids to promote normal brain development and healthy growth.

It is still another principal object of the present invention to increase the concentration of omega-3 fatty acid (docosahexaenoic acid) (DHA) within poultry eggs through a feeding regime provided to egg producing hens.

It is still another principal object of the present invention to increase the concentration of omega-6 fatty acids (arachidonic acid) (AA) within poultry eggs through a feeding regime provided to egg laying hens.

It is still another principal object of the present invention to improve the efficiency of acquisition of desired egg fractions through a combination acqueous extraction process to selectively remove phospholipid from egg yolks and a feeding regime process to increase the concentration of omega-6 (AA) and omega-3 (DHA) fatty acids.

It is still another principal object of the present invention to obtain a ratio of AA to DHA of between 1 to 1.3 to 4.

A feature of the present invention is the breaking of a poultry egg shell for removal of the contents.

Another feature of the present invention is the provision of the separation of the egg yolk from the albumen.

Still another feature of the present invention is the dilution of egg yolk material with water.

Still another feature of the present invention is the thorough mixing of the egg yolk material with water to dilute the egg yolk (DY).

Still another feature of the present invention is the adjustment of the pH of the mixed egg yolk and water material using acids/bases and/or salts.

Still another feature of the present invention is the exposure of the pH adjusted and mixed solution of egg yolk material and water to gravitational forces for separation through use of a centrifuge.

Still another feature of the present invention is the separation of a supernatant (DYS) fraction from the diluted and centrifuged DY fraction.

Still another feature of the present invention is the separation of a precipitate (DYP) fraction from the diluted and centrifuged DY fraction.

Still another feature of the present invention is the addition of viscosity agents such algin to the DYS fraction.

Still another feature of the present invention is the addition of carboxymethylcellulose to the DYS fraction.

Still another feature of the present invention is the blending of the DYS fraction with the viscosity agents and/or carboxymethylcellulose.

Still another feature of the present invention is the exposure of the blended DYS fraction and viscosity agents and/or carboxymethylcellulose to centrifuge separation.

Still another feature of the present invention is the separation of a cream CMC P fraction from the blended and centrifuged DYS fraction and viscosity agents and/or carboxymethylcellulose.

Still another feature of the present invention is the separation of a subnatant CMC fraction from the blended and centrifuged DYS fraction and viscosity agents and/or carboxymethylcellulose.

Still another feature of the present invention is the preliminary method of a hen feeding regime where hens are fed extruded whole fat soy beans from 0–100 lbs. per ton of feed with or without 50 lbs. per ton of flax seed additive.

Still another feature of the present invention is the isolation of the majority of the proteins of the pH adjusted and mixed egg yolk and water solution into a sludge material following exposure to gravitational forces through the utilization of a centrifuge.

Still another feature of the present invention is the further use of the sludge material which occurs following the pH adjustment and centrifuged exposure, where the sludge may be reconstituted with water or dried to provide functional egg yolk powder.

Still another feature of the present invention is the isolation of the supernatant within an aqueous solution as separated from the sludge when the supernatant contains the egg lipids and phospholipids with small amounts of protein.

DETAILED DESCRIPTION OF THE PREFERRED EMBODIMENT

In the past, methods have been utilized for separation of immunoglobulins (IgY) from egg yolks. These methods have focused upon the isolation of the immunoglobulins (IgY) having high activity. These methods have been modified and utilized to separate and isolate egg yolk phospholipids from the egg yolks. The separation of egg yolk phospholipids from egg yolks have attempted to provide an efficient method for extraction of high quality egg yolk phospholipids with a fully functional egg protein byproduct, an efficient methodology to accomplish this goal has not before been known in the art.

The present methodology for separation of high quality egg yolk phospholipids with a fully functional egg protein byproduct occurs through the acquisition of farm packed, ungraded, washed, fresh eggs where the egg yolks and whites may be separated by hand or mechanically.

The separated egg yolks then form the starting material for the aqueous extraction process to selectively remove phospholipids from the egg yolks. In general, the egg yolks may be uncooked or pasteurized as starting material for the aqueous extraction process.

First, the starting egg yolk material is preferably mixed with a 3.7 fold volume of water and preferably distilled water to form a diluted egg yolk fraction hereinafter referred to as DY. The dilution of the egg yolk material with water and mixing assists in the disruption of the egg yolk granule which is formed of a lipid-protein complex.

The diluted mixed egg yolk material is then centrifuged. The preferred rate of centrifuge exposure is 10,000×g, however, faster or slower rotational parameters may be utilized at the preference of an individual. The time of centrifuge exposure may vary dependent upon the type of centrifuge, rate of rotation and the volume of material to be centrifuged. When a rotation speed of 10,000×g is utilized the time of rotation is approximately 15 minutes. The temperature of the diluted mixed egg yolk material during centrifuge exposure is approximately 4° C.

Following centrifugation the diluted egg yolk material is separated into a supernatant aqueous phase hereinafter referred to as DYS and a viscous precipitate phase hereinafter referred to as DYP. Preferably the DYS fraction has a bright yellow-orange appearance and the DYP fraction has a dense white-yellow tinge. Following centrifugation the DYS fraction may be decanted from the DYP fraction which is high in protein. The DYP fraction may then be discarded or used for other purposes as desired by an individual. The separation or decanting of the DYS fraction from the DYP fraction concludes the first stage of the aqueous extraction process to selectively remove phospholipids from egg yolks.

The second stage of the aqueous extraction process generally involves the separation of the lipids from the DYS fraction. The second stage initiates with the addition of viscosity agents such as algin and high viscosity grade carboxy methylcellulose to the DYS fraction. Preferably a viscosity agent such as sodium alginate is added to achieve a final concentration of 0.1% alginate in the DYS fraction. The alginate may be added dry or as a diluted solution. Alternatively, carboxy methylcellulose (CMC) solution diluted to 0.15% is mixed with the DYS and sodium alginate solution in a ratio of 1-1 volume to 15 volume.

Next, the DYS with viscosity agent, is preferably exposed to centrifuge separation techniques. The parameters for centrifuge exposure are preferably 10,000×g for approximately 15 minutes at a temperature of 4° C. It should be noted that the parameters for centrifuge exposure identified herein have been provided for illustrative purposes only and may vary considerably dependent upon the type of centrifuge, volume of material to be separated, the rotational velocity of the centrifuge, and temperature parameters selected. The centrifuge procedure at this step preferably yields a cream layer over an aqueous solution. The cream layer and subnatant for the CMC separation contain approximately 40.2% and 0.13% fat, respectively, with the cream layer accounting for approximately 22% of the total volume. The cream and subnatant of the algin separtion contains approximately 35.5% and 1.3% fat, respectively, with the cream layer accounting for approximately 13% of the total volume. The performance of the aqueous extraction process to selectively remove phospholipids from egg yolk may be evaluated for verification according to the process of FIG. 2.

Figure 2:
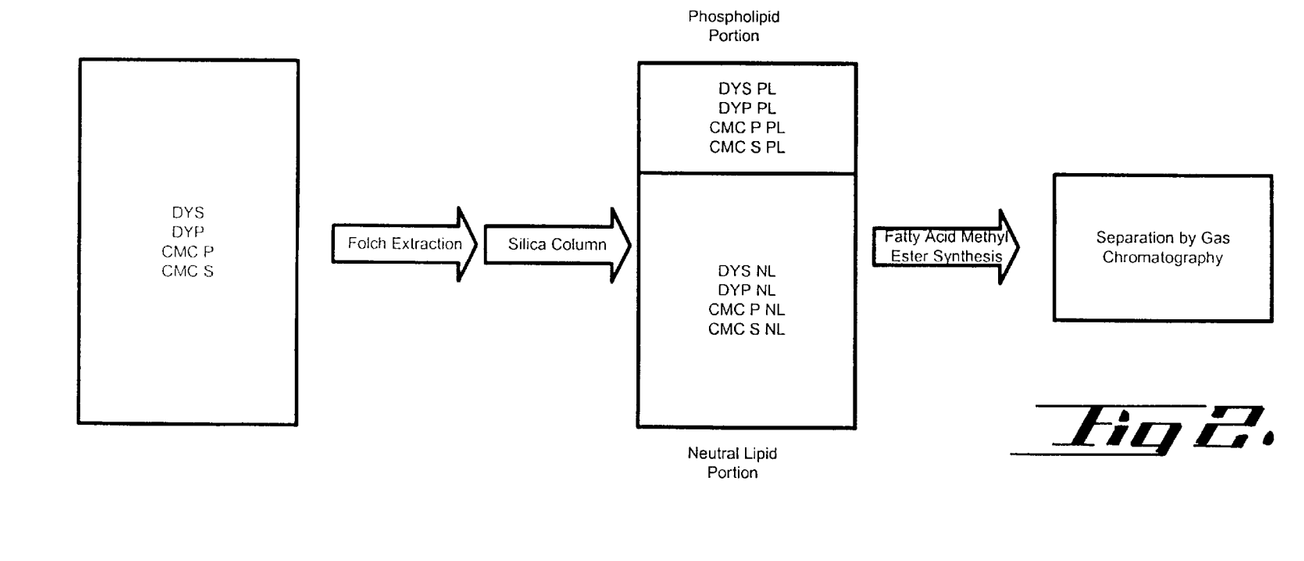
FIG. 2 shows the extraction of neutral and polar lipids from egg yolk fractions.

In FIG. 2 lipids from each the DYS, DYP, cream layer (CMC P), and the subnatant aqueous solution (CMC S) fractions were then extracted for analysis using a Folch extraction procedure. The Folch extraction procedure uses chloroform and methanol to extract lipids from a sample. The chloroform methanol solvent solutions may contain 0.1% butylated hydroxy toluene (BHT) (w:v) as an antioxidant. The sample desired for evaluation was then blended with 50 mL of chloroform methanol at a ratio of sample to chloroform methanol being 2 to 1 volume to volume for 1 minute. The blended slurry was then filtered. The filter cake was then re-extracted with another 50 mL of combined sample and chloroform methanol. The filtrate was then transferred to a suitable vessel where a 20% volume of 0.88% potassium chloride solution (aq) was added to the vessel. The resulting mixture was then allowed to stand overnight at a temperature of approximately 4° C.

The lower phase of the mixture was then removed and dried with sodium sulfate. The solvent was filtered through the vessel and rinsed with a chloroform methanol solution. This second filtrate was then transferred to another vessel where the solvent was removed by a roto-vap. The lipid was then dissolved in approximately 20 ml of chloroform methanol at an approximate ratio of lipid to chloroform of 20 to 1 volume to volume.

The resulting lipid extracts were then separated using a silica column. The use of a silica column involves the absorption of the sample liquid extract into a SepPak cartridge as may be available from Waters located in Millford, Maine. During this procedure neutral lipids were desorbed with 10 ml of chloroform methanol in a ratio of 20 to 1 sample liquid extract to chloroform methanol. The polar lipids were eluted with 10 ml of chloroform methanol at a 1 to 1 ratio followed by 20 ml of methanol. Both the neutral and polar lipids were then diluted to a standard volume of 50 ml and 25 ml respectively.

Next, fatty acid methylesters (FAMES) were formed from both the neutral and polar lipids. A sample of each neutral and polar lipid was next added to a separate reaction vessel. To each vessel was added boron trifluoride and an internal standard ($C_{17}$:1 fatty acid; 0.456 ug/ul). Each vessel was then inverted and heated to a temperature of approximately 100° for 30 minutes. Next, 26.4% of saturated NaCL sodium chloride solution was added to each reaction vessel. The FAMES were then extracted with hexane.

The FAMES were next separated through gas chromatography techniques which utilize a capillary column and having a temperature range of 110 to 230° C. at 5° C. per minute with a 1 minute final hold. The gas chromatography techniques identified peaks which were quantitative using standard peak area and response factors for each peak.

The verification procedure showed that the initial yolk consisted of 33.6% lipids. The aqueous extraction process to selectively remove phospholipids from egg yolks including generally dilution, followed by centrifuge separation yield an equal concentration of lipid for each of the DYS and DYP fractions. The DYS fraction comprised 84% by volume of the original DY diluted yolk which in turn represents an 82.8% recovery of the lipids from the DY fraction. Further extraction of the lipid from the DYS fraction using viscosity agents provided a cream formation. The CMC recovery step yielded a greater recovery of the lipids 82.5% of the original lipid recovered with the CMC gel with less lipid remaining in the subnatant (CMCS).

The verification procedures confirmed that the aqueous extraction process to selectively remove phospholipids from egg yolks through the use of a two stage separation procedure yielded cost effective lipid and protein rich fractions.

EXAMPLE 1

Figure 1:
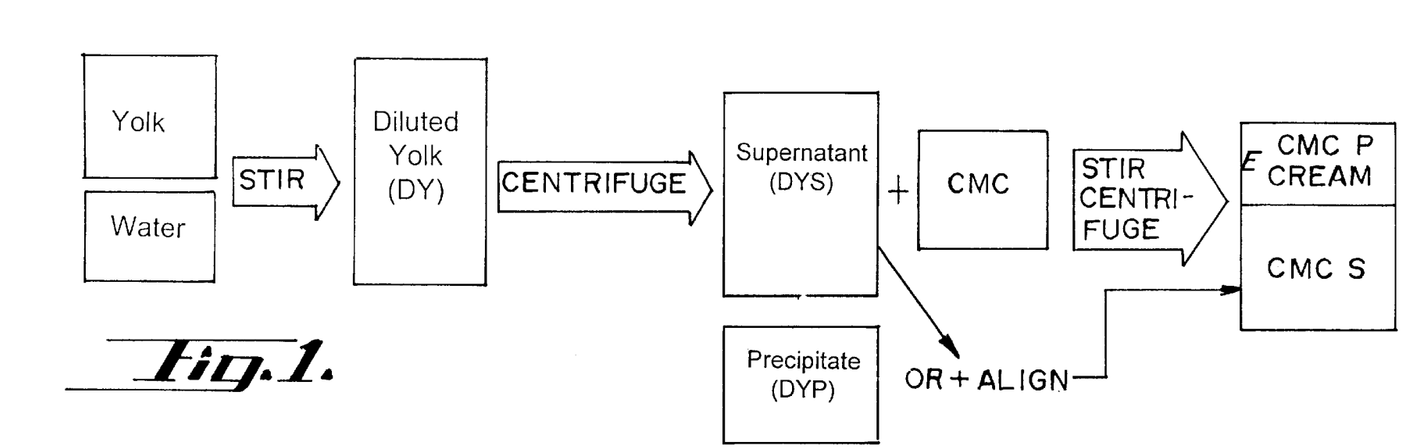
FIG. 1 is an overview of a yolk separation procedure using CMC and algin.

In general, the overview method for separation of phospholipids from the egg yolk is identified in FIG. 1. The separated egg yolks were mixed in one liter beakers with equal volumes of distilled water to form a diluted egg yolk fraction identified as (DY). This diluted egg yolk fraction was then covered and held overnight at a temperature of 4° C. The dilution of the egg yolks with water and mixing aided in the disruption of the egg yolk granule which is composed of a lipid-protein complex. The stock diluted egg yolk fraction (DY) was held and used over a three day period of time for separation.

Various dilution ratios are available when adding distilled water to the separated egg yolk material. In general, the dilution ratios for distilled water range from one part egg yolk to one to 7.4 parts distilled water. In addition, various pH ranges may be utilized to adjust the pH and salt content of the mixed distilled water and egg yolk material. For example, the pH of the mixed egg yolk material and distilled water may be adjusted to range from 5 to 9 thorough the use of 1.0N of NaOH. The separation of the phospholipids, in the supernatant, is enhanced at higher pH ranges. Therefore, the range of pH between 5 and 9 enhances the separation of the phospholipids as compared to separation techniques at pH ranges of 4 to 7.

The diluted egg yolk fraction, DY, was poured into 250 mL centrifuge bottles. The centrifuge bottles were sealed and centrifuged at 10,000×g for a period of time of 15 minutes at 4° C. The centrifuge technique employed resulted in a two phase separation with a supernatant aqueous phase (DYS) and a viscous precipitate phase (DYP). The supernatant aqueous phase (DYS) fraction was a bright yellow orange while the viscous percipitate phase (DYP) had a dense white-yellow tinge. The DYS fraction was decanted from the DYP fraction to effect separation. The DYP fraction, high in protein, was then discarded.

Separation of the phospholipids and/or lipids from the supernatant aqueous phase (DYS) fraction occurred through use of viscosity agents such as algin (Kelgin XL/F, Nutrasweet Kelco Company, Chicago, Ill.) and high viscosity carboxy methylcellulose (CMC) (Sigma Chemical Company, St. Louis, Mo.). Sodium alginate was added at 0.1% directly to the supernatant aqueous phase (DYS) and mixed with a warring blender. A 0.15% carboxy methylcellulose (CMC) solution was mixed with the DYS at a 1 to 1 ratio. A transfer method was sufficient for adequate mixing of the DYS and the CMC solution. The resulting slurries were separated using a centrifuge technique at 10,000×g for 15 minutes at 4° C. Both methods, algin and CMC, resulted in a separation of a cream layer over an aqueous solution.

The lipid and/or phospholipid content of each fraction was then quantitated through use of a standard monjonier procedure using a 5 gram sample carried out in duplicate.

The specific gravity (sg) was estimated by the weight of a 25 mL aliquot of each fraction.

An overview of the lipid extraction and separation procedure is given in FIG. 2. The lipids or phospholipids were then extracted using a Folch extraction procedure. The resultant lipid/phospholipid extracts were separated using a silica column and then fatty acid methyl ester derivatives were synthesized. These were injected onto a capillary gas chromatograph and were quantitated using authentic standards and response factors.

The Folch extraction procedure uses chloroform and methanol to extract lipid/phospholipids from the sample. The chloroform methanol solvent solutions contain 0.1% BHT as an antioxidant. An aliquot of the DYS and viscosity agents sample was blended in a sorval blender cup with 50 mL of chloroform methanol at a 2 to 1 ratio volume to volume (2:1 v:v) for one minute. The slurry was filtered through a Whatman 42 with a Buchner funnel. The filter cake was reextracted with another 50 mL of chloroform methanol with the filtrates combined, The filtrate was transferred to a 250 mL separatory funnel. A 20% volume of a 0.88% potassium chloride solution (aq) was added. The mixture was allowed to stand overnight at 4° C. The lower phase was removed and dried with sodium sulfate. The solvent was filtered through a Whatman 42 and the flask rinsed with chloroform methanol solution. This filtrate was analytically transferred to a 200 mL round bottom flask. The solvent was removed using a roto-vap. The lipid/phospholipid was dissolved in 20 mL of chloroform methanol at a 20 to 1 ratio volume to volume (20:1 v:v).

The sample was then absorbed onto a silica SepPak cartridge, (Waters, Milford, Massachusetts). The neutral lipids were desorbed with 10 mL of chloroform methanol at a 20 to 1 volume to volume (20:1 v:v). The polar lipids/phospholipids were then eluted with 10 mL chloroform methanol at a 1 to 1 ratio volume to volume (1:1 v:v) followed by 20 mL of methanol. The neutral and polar lipids/phospholipids were then diluted to a standard volume of 50 mL and 25 mL, respectively.

Fatty acid methylesters (FAMES) were formed for both the neutral and polar lipids. A sample (1 mL) of the FAMES was added to a reaction tube. Two mL of boron trifloride and an internal standard (C17:1 fatty acid, 0.456 ug/uL) were added to the tube. The tube was sealed and inverted and then heated at 100° C. for 30 minutes. Four mL of a saturated (26.4%) of sodium chloride solution were added to each tube. The FAMES were then extracted with 2 mL of hexane.

The FAMES were separated on a gas chromatograph (Varian 5890) with a DB-23 capillary column (J&W Scientific, Folsom, Calif.) using a temperature program of 110–230° C. at 5° C. per minute with a 1 minute final hold. Peaks were identified using authentic standards (New Chek Prep, Elysian, Mo.) and quantitated using the standard peak area and response factors (relative to C17:1) for each peak. Response factors for C18:2, C20:3, and C22:6 were calculated with the remainder estimated, Centrifugation uses differences in specific gravity to separate materials using centrifugal force. The specific gravity (sg) of each of the measured fractions is given in Table 1. The larger the differences of specific gravity of the two phases, theoretically, the easier the two phases will separate.

TABLE 1

Specific Gravity of Egg Yolk Fractions

| ID | Component Name | Specific Gravity (g/cc) |
|---|---|---|
| A | Yolk | 1.034 |
| B | Dilute Yolk (DY) | 1.017 |
| C | Diluted Yolk Supernatant (DYS) | |
| D | Diluted Yolk Precipitate (DYP) | 1.026 |
| E | CMC Cream (CMCP) | .0996 |
| F | CMC Subnatant (CMCS) | 1.014 |

Lipid/phospholipid contents of each fraction are given in Table 2. The initial yolk consisted of 33.6% lipids/phospholipids. Dilution with distilled $H_2O$ followed by centrifugal separation resulted in an equal concentration of lipid in each of the fractions, DYS and DYP. Since DYS comprised 84% by volume of the original DY, this represents an 82.8% recovery of lipid from DY, Extraction of the lipid/phospholipid from DYS using the viscosity agents resulted in a cream formation. The CMC resulted in a greater recovery of the lipid (82.5% of the original lipid recovered with the CMC gel) with less lipid remaining in the subnatant (CMCS).

TABLE 2

Tracking of Lipid in Yolk Separation Procedure Starting With 1000 Milliliters Yolk

| ID | Component Name | Lipid Content | Volume (mL) | Lipid Recovery |
|---|---|---|---|---|
| A | Yolk | 33.6% | 1000 | 100% |
| B | Dilute Yolk (DY) | 16.8% | 2000 | 100% |
| C | Diluted yolk Supernatant (DYS) | 16.6% | 1680 | 82.8% |
| D | Diluted Yolk Precipitate (DYP) | 18.2% | 320 | 17.2% |
| E | CMC Cream (CMCP) | 40.2% | 740 | 82.5% |
| F | CMC Subnatant (CMCS) | 0.13% | 2620 | 0.3% |
| G | Algin Cream | 35.5% | 218 | 23.0% |
| H | Algin Subnatant | 1.3% | 1462 | 5.7% |

The fatty acid composition of each fraction is provided in Table 3. The loss of the fatty acids is of similar magnitude across the various fractions. The reduction of the fatty acids across the various fractions of similar magnitude shows the absence of a solubility phenomenon and the existence of a possible physical or entrapment phenomenon.

The omega-3 fatty acids are distributed in a 1 to 3 ratio 1:3 between the neutral and polar lipid/phospholipid classes. The overall yield of the omega-3 fatty acids appears to 80% to 90%.

The disclosed method shows the extraction process consisting of a two stage separation procedure to yield a lipid/phospholipid and protein rich fraction. The first separation step is critical to recovery. The first separation step is where a majority of the lipid is lost. The second step, using CMC recovery, captures approximately 99% of the lipid/phospholipid from the DYS fraction. Fractionation of lipid changes with alterations to the dilution method may also be considered. Constant agitation of the DYS fraction may help to dissociate the yolk granules and increase the lipid yield. Additionally, considerations related to scale may be implemented to promote efficiencies to satisfy bulk production requirements.

at 146° F. The temperature ranged from 149 to 146° F. The flow rate was regulated at 232 pounds per minute. The hold time was set at 5.4 minutes. The product was packaged in 30 pound plastic tubes with plastic liners sealed with rubber bands.

The product was pasteurized and transferred by refrigerated truck for processing one day later. The product temperature was 60° F. upon receipt for testing.

The egg yolk was then transferred from tubs into a holding vat. The product was mixed with 1500 pounds of distilled water. The product was then thoroughly mixed with the resulting mixture being cooled to 34° F. in five hours and being held at this temperature overnight.

The diluted egg yolk material was then transferred from the holding tank to 10 gallon milk cans using a centrifugal pump. The cans were heated to 140° F. in a water vat tank intended for pasteurizing cream. Once the material had been heated, it was transferred to a 50 gallon jacketed tank. The diluted egg yolk was held at 140° F. for approximately 60

TABLE 3

Fatty acid composition of each fraction and % recovery for CMC precipitate

| ID | 14:0 | 14:1 | 16:0 | 16:1 | 18:0 | 18:1 | 18:2 | 18:3 | 20:1 |
|---|---|---|---|---|---|---|---|---|---|
| Retention Time (min) | 9.44 | 10.06 | 12.65 | 13.11 | 15.75 | 16.11 | 16.86 | 17.77 | 19.03 |
| Response Factor | 0.76 | 0.8 | 0.92 | 0.96 | 1.02 | 1.05 | 1.08 | 1.2 | 1.5 |

| Amount (g) FA/1,000 g original starting material | | | | | | | | | |
|---|---|---|---|---|---|---|---|---|---|
| Initial Yolk | 0.93 | 0.14 | 93.45 | 7.95 | 33.66 | 123.72 | 51.83 | 0.81 | 0.88 |
| DY Supernatant N | 0.51 | 0.12 | 35.64 | 4.76 | 10.78 | 63.41 | 20.91 | 0.54 | 0.53 |
| DY Supernatant P | 0.27 | 0.00 | 44.47 | 1.84 | 16.98 | 36.60 | 21.66 | 0.12 | 0.19 |
| Total | 0.78 | 0.12 | 80.11 | 6.60 | 27.77 | 100.01 | 42.56 | 0.66 | 0.72 |
| DY Precipitate N | 0.10 | 0.01 | 4.08 | 0.93 | 2.96 | 13.63 | 4.90 | 0.10 | 0.11 |
| DY Precipitate P | 0.05 | 0.01 | 9.25 | 0.42 | 2.94 | 10.08 | 4.37 | 0.05 | 0.05 |
| Total | 0.15 | 0.01 | 13.33 | 1.35 | 5.90 | 23.71 | 9.26 | 0.15 | 0.16 |
| CMC liquid N | 0.00 | 0.00 | 0.37 | 0.00 | 0.00 | 0.50 | 0.00 | 0.00 | 0.00 |
| CMC liquid P | 0.00 | 0.00 | 0.25 | 0.00 | 0.13 | 0.75 | 0.13 | 0.00 | 0.00 |
| Total CMC liquid | 0.00 | 0.00 | 0.62 | 0.00 | 0.13 | 1.25 | 0.13 | 0.00 | 0.00 |
| CMC Precipitate N | 0.58 | 0.00 | 38.30 | 4.82 | 11.97 | 63.83 | 21.74 | 0.48 | 0.44 |
| CMC Precipitate P | 0.00 | 0.00 | 45.15 | 2.36 | 17.02 | 45.64 | 22.47 | 0.00 | 0.00 |
| Total CMC Precip | 1.20 | 0.00 | 83.86 | 7.79 | 29.34 | 109.98 | 44.63 | 1.06 | 0.95 |
| % yield | 128.77% | 0.00% | 89.74% | 97.98% | 87.16% | 88.90% | 86.11% | 131.29% | 107.67% |

| ID | 20:2 | 20:4 | 22:4 | 22:3 | 22:6 |
|---|---|---|---|---|---|
| Retention Time (min) | 19.76 | 20.46 | 23.19 | 23.29 | 24.26 |
| Response Factor | 1.6 | 1.8 | 1.85 | 1.86 | 1.88 |

| Amount (g) FA/1,000 g original starting material | | | | | |
|---|---|---|---|---|---|
| Initial Yolk | 1.06 | 15.44 | 0.39 | 1.34 | 4.90 |
| DY Supernatant N | 0.38 | 0.00 | 0.27 | 0.76 | 0.84 |
| DY Supernatant P | 0.53 | 12.79 | 0.00 | 0.00 | 3.49 |
| Total | 0.91 | 12.79 | 0.27 | 0.76 | 4.33 |
| DY Precipitate N | 0.11 | 1.26 | 0.09 | 0.41 | 0.40 |
| DY Precipitate P | 0.05 | 1.39 | 0.83 | 0.17 | 0.17 |
| Total | 0.15 | 2.64 | 0.12 | 0.58 | 0.57 |
| CMC liquid N | 0.00 | 0.00 | 0.00 | 0.00 | 0.00 |
| CMC liquid P | 0.00 | 0.08 | 0.00 | 0.00 | 0.00 |
| Total CMC liquid | 0.00 | 0.08 | 0.00 | 0.00 | 0.00 |
| CMC Precipitate N | 0.18 | 3.84 | 0.00 | 1.18 | 1.07 |
| CMC Precipitate P | 0.00 | 9.56 | 0.00 | 2.89 | 2.55 |
| Total CMC Precip | 0.35 | 13.64 | 0.00 | 4.95 | 3.85 |
| % yield | 32.94% | 88.38% | 0.00% | 369.26% | 78.48% |

EXAMPLE 2

On scale production, fifteen hundred (1500) pounds of pasteurized egg yolk protein were obtained from M. G. Waldbaum, Wakefield, Nebr. The product was pasteurized on a commercial pasteurizer which is fed by a positive displacement pump and has 432 feet of 3 inch diameter holding tubes. The indicating thermometer was documented minutes, The material was transferred using positive displacement pumps to a Westfalia SE-7 continuous centrifuge at 2.5 liters per minute with 50 pounds per square inch back pressure. Examples of centrifuge settings are shown in Table 4.

TABLE 4

Examples of Westfalia SB-07 Settings During operation.

| PLC | | Time | | |
|---|---|---|---|---|
| Process Event Number | | 0630 | 1015 | 1530 |
| 901 | Process Timer - Bowl Shoot (min.) | 6 | 7 | 7 |
| 903 | Partial Counter - # partial shoots before full | 5 | 5 | 5 |
| 905 | Bowl open(s) | 3 | 3 | 3 |
| 906 | Partial Feed - Interrupt time(s) | 5 | 5 | 5 |
| 907 | Partial Flush Water(s) | 2 | 1 | 1 |
| 912 | Full Feed Interrupt - (s) | 20 | 20 | 20 |
| 913 | Full Flush - Water(s) | 4 | 4 | 4 |

The sludge material (protein) was collected into sanitized 10 gallon milk cans and cooled in an ice water bath. The material was then spray dried using a Coulter Spray Drier which has a nominal evaporation rate 90 lb. water per hour. The drier was fed with a Gallan high pressure pump with a Spraying Systems nozzle and insert. The spray conditions were: inlet temperature 350° F.; outlet temperature 160° F.; feed pressure 1000 psi. Approximately 60 lbs. of material were spray dried. An additional 33 lbs. were dried six days later.

The solids of the feed material, sludge (protein) and concentrate (lipid rich phase) are shown in Table 5.

TABLE 5

Solids Content of the Fractions Collected

| | Time | | |
|---|---|---|---|
| Fraction | 0630 | 1015 | 1530 |
| Solids - Sludge (Protein) % | 23.4 | 33.2 | 29.2 |
| Solids - Concentrate (Lipid) % | | 18.9 | |
| Solids - Feed % | 22.1 | 22.1 | 22.1 |

Spray drying the protein phase resulted in approximately 100 lbs. of dried material. Fifty (50) pounds of the material from the initial drying date were packaged in 12.5 Lb. quantities into lined plastic tubs. Each tub was sampled and the analysis for a composite sample is shown in Table 6. Microbiological data was collected on each sample and the averages are shown in Table 7.

TABLE 6

Analytical Analysis of Spray Dried Egg Yolk Protein Extract

| | % | Method |
|---|---|---|
| Protein | 56.54 | Kjeldahl |
| Fat | 33.59 | Acid Hydrolysis |
| Moisture | 4.01 | Vacuum Oven |
| CHO & Ash | 5.86 | By Difference |

TABLE 7

Microbiological Results

| Test | |
|---|---|
| SPC | 1300 CFU/gm |
| Yeast & Mold | a10 CFU/gm |
| Salmonella | Negative |

The fat content of the dried product is higher than the bench-scale extractions. This is partially a result of contamination of the sludge with the supernatant portion realized during desludging. Additionally, as the egg yolk ages, it is more difficult to separate. The yolk conducted within the batch separation techniques was five days old (minimum) and experienced temperature fluctuation. Fresher yolk and better control of the processes yield greater protein to fat ratios.

EXAMPLE 3

In an additional embodiment, a gentle batch pasteurization process was utilized to effect subsequent separation of the yolk at two different temperatures.

Initially, egg yolk was diluted in a ratio of one to one volume to volume 1:1 with distilled water. Two one gallon jugs were filled with the diluted and mixed material. Both jugs were lowered into a water bath at 60° C. (140° F.). A water bath having a temperature of 50° C. or higher may also be utilized at the discretion of an individual. A come-up time of 30 minutes was allowed followed by a one hour hold. The two samples were then removed from the water bath. One was immediately separated while the other was placed into an ice water bath to cool. The cooled sample was reduced to a temperature of 40° F. Each sample was centrifuged at 10,000x.9 for 15 minutes including spin up time. The supernatant and sludge were collected and analyzed for protein, fat and total solids.

Both samples separated during centrifugation. The sample which was centrifuged hot yielded a more compacted pellet, while the cooled sample was less packed and was more difficult to distinctly separate into two phases.

The sample which was separated hot resulted in higher solids than the corresponding cold fractionated sample. The hot fractionation resulted in a better separation with less protein in the supernatant and more in the sludge as seen in the protein/fat and fat/protein ratios of Table 8.

TABLE 8

Analytical Analysis of the Separated Fractions

| | Separation Temp. | | | | |
|---|---|---|---|---|---|
| | Hot (140° F.) | | Cold (40° F.) | | |
| | Supernatant | Sludge | Supernatant | Sludge | Yolk |
| Protein | 5.39 | 27.85 | 5.21 | 25.55 | 14.9 |
| Fat | 13.79 | 12.23 | 13.06 | 12.21 | 27.5 |
| Solids | 20.33 | 42.52 | 19.31 | 39.98 | 44.0 |
| Dry Basis Protein | 26.5 | 65.5 | 27.0 | 64.1 | 33.9 |
| Fat | 67.8 | 28.8 | 67.6 | 30.6 | 62.5 |
| Ratio Protein/Ft | | 2.27 | | 2.09 | 0.54 |
| Fat/Protn. | 2.56 | | 2.50 | | 1.84 |

The batch pasteurization process resulted in material which could be separated using centrifugation. The hot separation resulted in a better phase separation in the samples than the cold separation. The protein/fat and fat/ protein ratios indicate that the hot separation resulted in better separation. This data shows that the hot separation is preferred to obtain a cleaner separation of the fat and protein from the egg yolk material.

Table 9 shows the cholesterol: DHA ratios for the various fractions which have been provided for the referenced value for dried commercial yolk and the cholesterol content as determined on the crude lipid extracts.

TABLE 9

Comparison of Cholesterol: DHA Ratios for Various Egg Fractions

|  | Cholesterol | DHA | Ratio/Cholesterol/DHL |
|---|---|---|---|
| Phospholipid 85% | 5.5 | 3.1 | 1.77 |
| Std. Egg Yolk Powder | 2.72* | 0.53 | 5.13 |
| Crude Lipid Extract 1 | 2.72** | 0.72 | 3.78 |
| Crude Lipid Extract 2 | 2.72** | 1.40 | 1.94 |

*Reference value for dried commercial yolk
**Estimate-Cholesterol content has not been determined on crude lipid extracts.

The aqueous extraction process to selectively remove phospholipids from egg yolks may be enhanced by controlling a specifically formulated feed which is supplied to the egg producing hens in order to enhance the quality of the eggs obtained.

The feeding regime begins with the provision of appropriate or preferred feed to the fowl which provide the eggs utilized in the aqueous extraction process to selectively remove the phospholipids from the egg yolks. The feeding regime may be important in so far as controlling the quality and quantity of the phospholipids in the eggs produced by the fowl. By controlling the feeding process the quality and quantity of eggs and thus the by-product described herein may be enhanced.

In general, the feeding regime facilitates the production of egg yolk having a specific fatty acid content for eggs and particularly increased levels of omega-6 fatty acid (arachidonic acid) (AA) and increased levels of omega-3 fatty acid (docosahexaenoic) (DHA) and finally a desired ratio of AA to DHA ranging from 1 to 1.3 to 4.

The feeding regime facilitates the production of eggs having a modified egg fatty acid content through the inclusion of extruded whole fat soy beans from 0 to 100 lbs per ton of feed with or without 50 lbs per ton of flax seed as fed to the fowl.

The rations containing the above identified volume of extruded whole fat soy beans and/or flax seed are fed to hens in a conventional manner where the hens receive conventional laying rations with appropriate adjustments in the rations to provide a desired content of essential nutrients and energy levels required to maintain egg production and body weight for the hens. Fatty acid composition of the egg fat is preferably modified within three weeks of the initiation of the feeding program of modified rations to the egg laying hens.

The above-described modified feeding regime is economical and generally results in an increased expense for feed of approximately $2.00 per ton of feed. The extruded whole fat soy beans and flax seed are readily available for mixture into standard feeding rations.

The feeding regime described herein does not require the specific handling, storage, or cooling of rations as would be required for fish oils or other supplements. In addition, the feeding regime utilizing extruded whole fat soy beans and/or flax seed does not produce off flavors or color in the resulting eggs or egg yolks.

In fact, nutritional research has suggested the benefits of supplementing infant formulas with DHA where performance is maximized when AA is utilized. Eggs are one of the best natural sources of AA.

EXAMPLE 4

Six dietary treatments were fed to five replicate pens with five Dekalb Delta Hens (36 weeks of age) per pen for a total of 15 weeks (to 51 weeks of age). The dietary treatments were:

1. Control
2. 50 lbs extruded soy beans;
3. 100 lbs extruded soy beans;
4. 200 lbs extruded soy beans;
5. 50 lbs extruded soybeans and 50 lbs flax; and
6. 100 lbs extruded soybeans and 50 lbs flax, per ton, respectively.

Dietary compositions and calculated nutrient analysis are given in Table 10. The balance of the dietary fat came from the animal-vegetable oil (A-V) blend fat supply.

Daily feed composition and egg production were recorded. Weekly egg samples were taken of one days production and egg weights and breakouts (albumin, yolk, and shell) were measured. Diet, fat, flax, and extruded soybean samples were sent to an analytic laboratory for fatty acid analysis on three occasions (August, September, and October). Starting the middle of October, all eggs were saved to obtain a large enough quantity to spray dry yolks at the IANR Food Processing Center, University of Nebraska. Nearly 20 lbs of yolks from each treatment were spray dried at the Food Processing Center early in December and yields were determined for treatments 2, 3, 4, 5 and 6. Diet 1 was used as the warm-up sample for the spray dryer and yield was not determined.

Figures 2, 4:
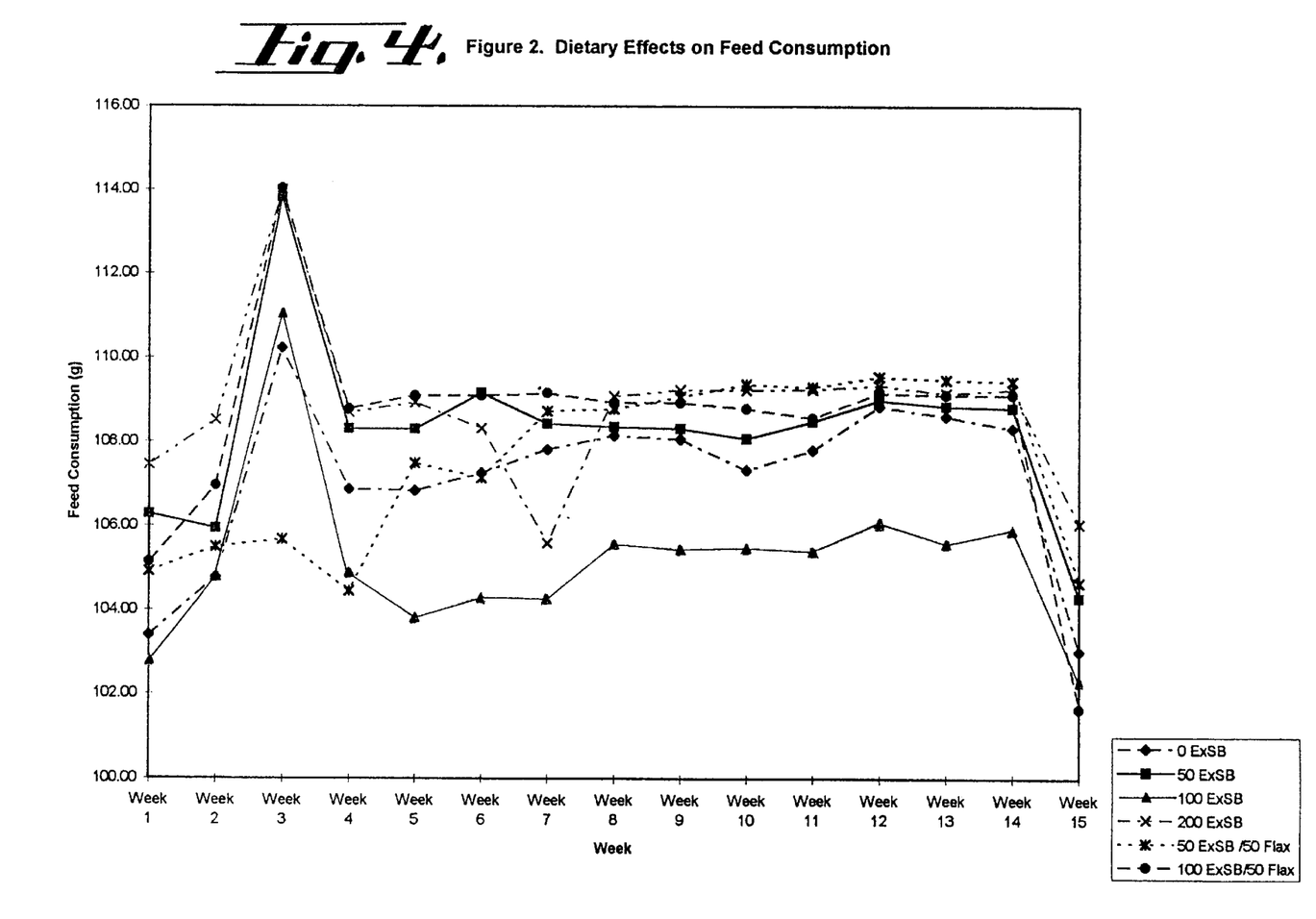
FIG. 4 shows dietary effects on feed production.
Figure 3:
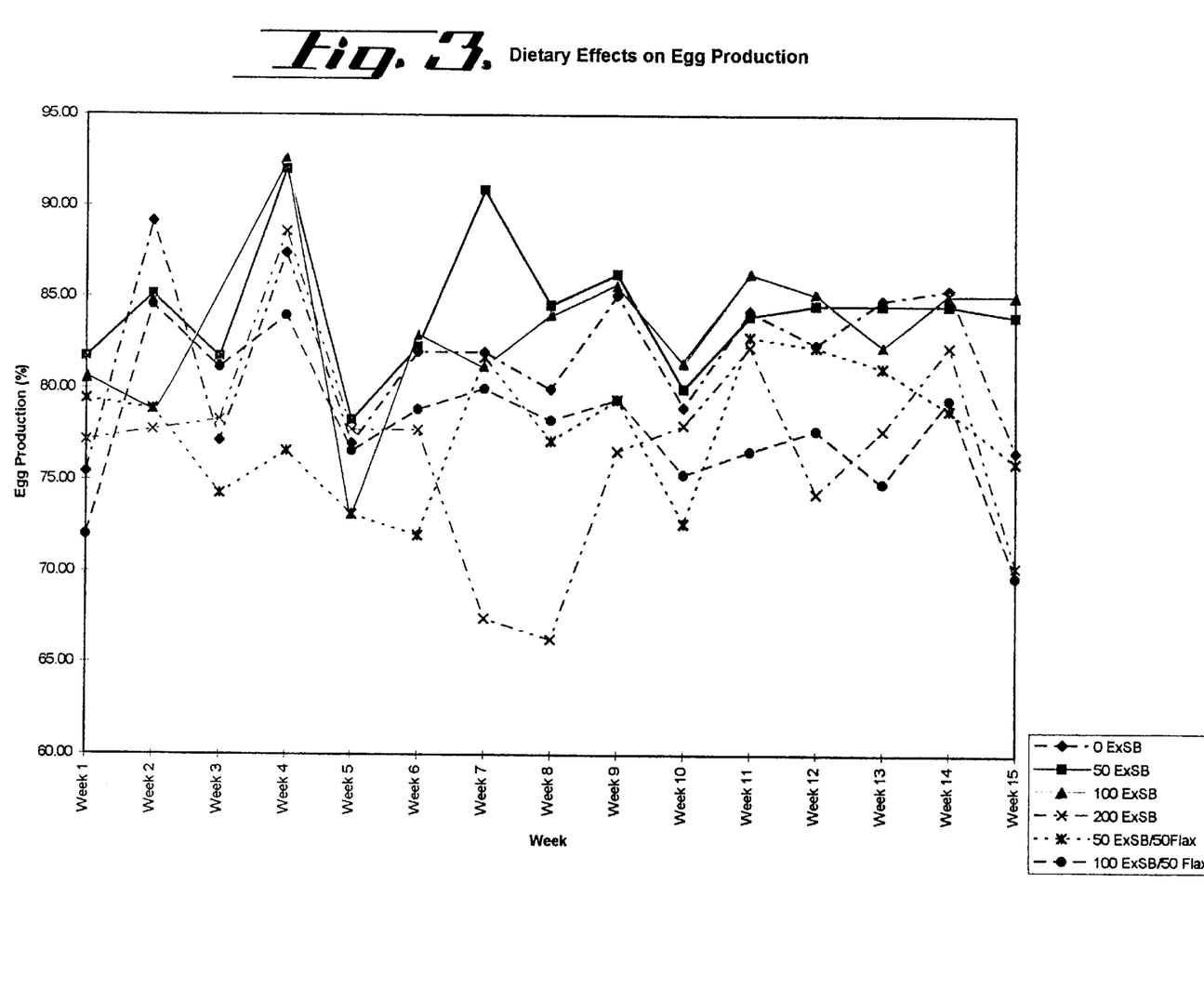
FIG. 3 shows dietary effects on egg production.
Figure 5:
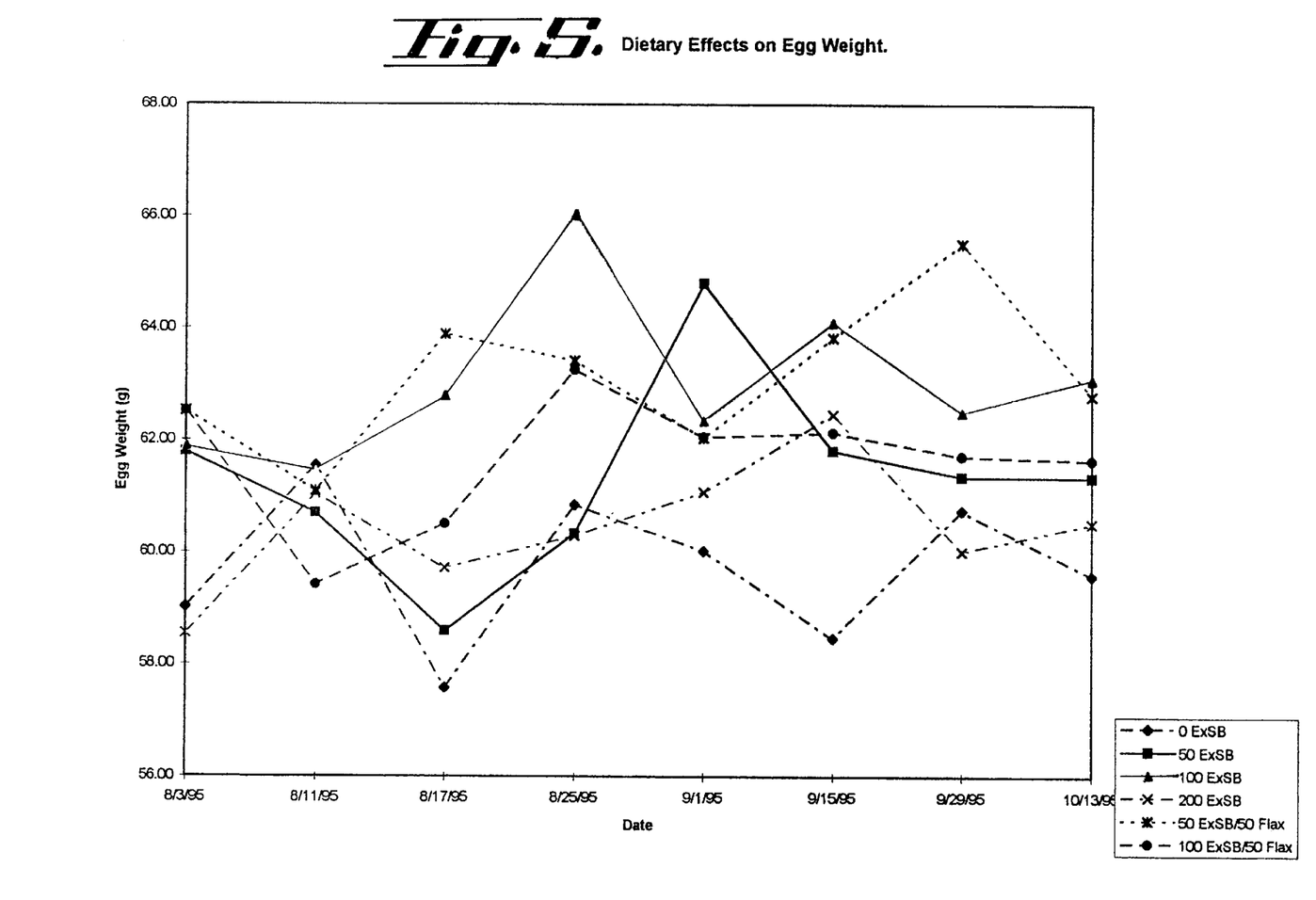
FIG. 5 shows dietary effects on egg weight.

Effects of dietary treatments on the production parameters of egg production, feed intake, and egg weight are given in Table 11 and FIGS. 3, 4 and 5 respectively. Dietary treatment effects on average egg production over the 15 week period show an overall enhancement of egg production by hens fed the 50 and 100 Lb levels of extruded soybeans compared to the control. A drop in production was observed in hens fed the highest level of extruded soybeans (200 lbs) of the combination treatments of extruded soybeans and flax compared to the control diet. The effect of the high levels of dietary extruded soybeans was not expected; however, a Trypsin inhibitor analysis of the extruded soybeans yielded unacceptably high results (22,200 TIU/g vs. a standard value of 8–10,000 TIU/g) indicating inadequate heating of the soybeans during the extrusion process. It appears that at the 200 Lb inclusion rate, the bird is effected by this high Trypsin inhibitor level to a point of depressing egg production and egg weight. The levels of egg production are comparable to a sister flock of birds which average 83% during this time period. Dietary treatments showed no marked effect on feed intake (FIG. 4 and Table 11) with the exception of the 100 Lb extruded soybean treatment group being an average of 2 grams less than the control group. Body weight (Table 11) showed normal weight gain over the 13 week period for the control and low dietary extruded soybeans (50 lbs) treatments. Higher dietary extruded soybeans (100 and 200 lbs) in treatments 3, 5, and 6 resulted in poor weight gain and in the case of diet 6, a small weight loss which may be the result of undercooking of the extruded soybeans.

Dietary effects on egg weight (FIG. 5 and Table 11) show fluctuation over time in the control treatment and several of the dietary treatments. It is interesting to note that despite a slight decrease in feed intake, birds on diet 3 (100 lbs extruded soybeans) had a consistently greater egg weight compared to the control or high level of extruded soybeans (200 lbs). Both extruded soybeans plus flax seed treatments (5 and 6) exhibited good egg size relative to the control. The only treatment that did not show increased egg size relative to the control was the highest level of dietary extruded soybeans inclusion (200 lbs per ton). This likely was due to the detrimental effect of Trypsin inhibitor on protein and amino acid digestibility. In past experiments with flax seed, a slight depression in egg weight has been observed. This combination of extruded soybeans with flax seed seems to have made up for this decrease.

Effects on dietary treatment on egg components (shell, white, and yolk) and percent spray-dried yolk yield are shown in Table 11. Interestingly, the proportion of white:yolk increased with dietary extruded soybeans and flax. It appears as the dietary treatments increase egg size, they also increase the proportion of albumin:yolk. Previous observations with the Delta have indicated that as egg size increases with age, the proportion of albumin:yolk increases. It appears dietary manipulation may produce the same effect as age in the Delta. Most interesting are the results of the spray dried yolk yields. The results from the spray dried yolk yields showed a marked effect of dietary fat source and yolk fatty acid composition on percent yields. As the level of extruded soybeans and flax increase, the spray dried yolk yield increased.

Table 12 shows the dietary effects of egg yolk fatty acid composition of the egg sampled in early October. The inclusion of extruded soybeans has an obvious effect increasing the content of C18:2, and C22:6 in egg yolk while maintaining levels of C20:4. Flax seed increased the C18:3, and C22:6 content of the egg yolk. The sought after ratio of 2.0–3.0 of C20:4:C22:6 was accomplished with diets 2, 3, and 4. Inclusion of dietary flax brings the ratio down to less than 2.0 due to higher levels of C22:6 in the flax fed hen yolks.

The present invention may be embodied in other specific forms without departing from the spirit of essential attributes thereof; and it is therefore, desired that the present embodiment be considered in all respects as illustrative and not restrictive, reference being made to the foregoing description.

TABLE 10

Waldbaum Study 3 - Fat Source Effect on Egg Fatty Acid Composition and Efficiency of Egg Production - Dietary Compositions

| Ingredient | Diet (%) | | | | | |
| --- | --- | --- | --- | --- | --- | --- |
| | 1 | 2 | 3 | 4 | 5 | 6 |
| Corn | 54.6 | 54.6 | 54.6 | 54.6 | 54.0 | 54.0 |
| Soybean meal (47%) | 26.9 | 25.3 | 23.7 | 20.4 | 23.8 | 22.2 |
| Extruded beans | — | 2.5 | 5.0 | 10.0 | 2.5 | 5.0 |
| Flax | — | — | — | — | 2.5 | 2.5 |
| Oats | 2.5 | 2.5 | 2.5 | 2.5 | 2.5 | 2.5 |
| Corn gluten meal | .80 | .61 | .41 | .02 | .75 | .56 |
| A-V fat blend | 4.16 | 3.48 | 2.80 | 1.44 | 2.86 | 2.18 |
| Limestone | 6.9 | 6.9 | 6.9 | 6.9 | 6.9 | 6.9 |
| Oyster shell | 2.0 | 2.0 | 2.0 | 2.0 | 2.0 | 2.0 |
| Dical. Phos. | 1.62 | 1.61 | 1.61 | 1.59 | 1.61 | 1.60 |
| Salt | .34 | .34 | .34 | .34 | .34 | .34 |
| Vit/Min premix | .10 | .10 | .10 | .10 | .10 | .10 |
| Methionine | .09 | .08 | .08 | .08 | .08 | .08 |
| Total | 100.01 | 100.02 | 100.04 | 99.975 | 99.94 | 99.96 |
| Calculated Analysis | | | | | | |
| Protein, % | 17.0 | 17.0 | 17.0 | 17.0 | 17.0 | 17.0 |
| ME, kcal/kg | 2,865 | 2,865 | 2,865 | 2,865 | 2,865 | 2,865 |
| Ether extract, % | 6.80 | 6.62 | 6.44 | 6.08 | 6.86 | 6.86 |
| Calcium, % | 3.85 | 3.85 | 3.85 | 3.85 | 3.85 | 3.85 |
| Avail. Phos., % | .41 | .41 | .41 | .41 | .41 | .41 |
| Lysine, % | .90 | .91 | .92 | .95 | .90 | .92 |
| Methionine, % | .37 | .37 | .37 | .37 | .37 | .37 |
| TSAA, % | .70 | .70 | .70 | .70 | .70 | .70 |
| Tryptophan, % | .21 | .21 | .21 | .21 | .21 | .21 |
| Threonine, % | .69 | .70 | .70 | .70 | .70 | .70 |

TABLE 11

Waldbaum Study 3 - Fat Source Effect on Egg Fatty Acid Composition and Efficiency of Egg Production - Feed Consumption, Egg Production, Body Weights and Egg Yields

| Dietary Treatment | Feed Intake g/hen/day | Egg Production % | Body wt. Gain/Loss[1] g | Egg wt. g | % Shell | % Albumin | % Yolk | % Yolk dry yield[2] |
| --- | --- | --- | --- | --- | --- | --- | --- | --- |
| 1. Control | 107.2 | 81.9 | 43 | 59.7 | 12.79 | 60.84 | 26.26 | — |
| 2. 50 Ext SB | 108.3 | 84.3 | 48.2 | 61.3 | 13.28 | 60.39 | 25.89 | 40.3 |

TABLE 11-continued

Waldbaum Study 3 - Fat Source Effect on Egg Fatty Acid Composition and Efficiency of Egg Production - Feed Consumption, Egg Production, Body Weights and Egg Yields

| Dietary Treatment | Feed Intake g/hen/day | Egg Production % | Body wt. Gain/Loss[1] g | Egg wt. g | % Shell | % Albumin | % Yolk | % Yolk dry yield[2] |
|---|---|---|---|---|---|---|---|---|
| 3. 100 Ext SB | 105.2 | 83.3 | 3.0 | 63.0 | 12.49 | 61.24 | 25.67 | 42.5 |
| 4. 200 Ext SB | 108.8 | 76.8 | 7.0 | 60.5 | 12.53 | 61.45 | 25.82 | 43.7 |
| 5. 50 Ext SB/50 Flax | 107.6 | 77.8 | 24.4 | 63.1 | 12.57 | 61.55 | 25.46 | 53.7 |
| 6. 100 Ext SB/50 Flax | 108.4 | 77.9 | −23.0 | 61.7 | 12.54 | 61.44 | 25.61 | 44.3 |

[1]Body weight change from start of experiment to week 13.
[2]Yield on yolks spray dried at the IANR food processing center (12/5/95).

TABLE 12

Waldbaum Study 3 - Fat Source Effect on Egg Fatty Acid Composition and Efficiency of Egg Production - Egg Yolk Fatty Acid Composition

| Dietary treatment % | C14:0 | C10:0 | C16:1 | C18:1 | C18:0 | C18:1 | C18:2 | C18:3 | C20:1 | C20:4 | C22:0 | C22:6 |
|---|---|---|---|---|---|---|---|---|---|---|---|---|
| 1. Control | .43 | 26.9 | 2.19 | 36.1 | 11.0 | 1.65 | 17.1 | .50 | .17 | 2.88 | 0.00 | .88 |
| 2. 50 Ext SB | .39 | 27.8 | 2.37 | 35.2 | 10.7 | 1.60 | 17.2 | .42 | .18 | 2.93 | 0.00 | 1.03 |
| 3. 100 Ext SB | .36 | 27.3 | 1.99 | 34.5 | 10.6 | 1.53 | 19.1 | .50 | .16 | 2.79 | 0.00 | 1.09 |
| 4. 200 Ext SB | .36 | 26.6 | 1.88 | 33.1 | 11.1 | 1.37 | 20.8 | .67 | .16 | 2.71 | 0.00 | 1.10 |
| 5. 50 Ext SB/50 Flax | .38 | 27.2 | 2.41 | 33.8 | 10.7 | 1.52 | 17.6 | 1.62 | .13 | 2.27 | .13 | 1.96 |
| 6. 100 Ext SB/50 Flax | .33 | 26.6 | 2.01 | 33.7 | 11.4 | 1.38 | 18.1 | 1.40 | .13 | 2.60 | .16 | 2.14 |

| Dietary treatment % | w-3 LCP | w-6 LCP | SAFA | MUFA | PUFA | C18:2 w-6/C18:3w-3 | C20:4 w-6/22:6w-3 |
|---|---|---|---|---|---|---|---|
| 1. Control | 1.37 | 19.94 | 38.5 | 40.2 | 21.3 | 34.4 | 3.28 |
| 2. 50 Ext SB | 1.45 | 20.13 | 38.9 | 39.5 | 21.6 | 41.41 | 2.83 |
| 3. 100 Ext SB | 1.60 | 21.86 | 38.3 | 38.3 | 23.5 | 37.76 | 2.56 |
| 4. 200 Ext SB | 1.76 | 23.55 | 38.1 | 36.6 | 25.3 | 31.30 | 2.47 |
| 5. 50 Ext SB/50 Flax | 3.58 | 19.86 | 38.4 | 38.2 | 23.6 | 10.88 | 1.16 |
| 6. 100 Ext SB/50 Flax | 3.54 | 20.7 | 38.4 | 37.4 | 24.4 | 12.94 | 1.22 |

What is claimed is:

1. A method to selectively remove phospholipid from egg yolks comprising:
separating the egg yolk material from the remainder of egg;
diluting the egg yolk material with water;
mixing the diluted egg yolk material and the water;
adjusting the pH and salt content of the mixed egg yolk material and water;
separating the pH adjusted and mixed egg yolk material and water into various components by gravity exposure into a DYS fraction and a DYP fraction;
separating the DYS fraction from the DYP fraction; and
separating at least 1.5 percent of the phospholipid from the DYS fraction.

2. The method according to claim 1, the separating of lipids from the DYS fraction comprising adding viscosity agents to the DYS fraction.

3. The method according to claim 2 further comprising mixing of the DYS fraction and the viscosity agents.

4. The method according to claim 3, further comprising exposing the mixed DYS fraction and viscosity agents to centrifuge separation into a cream layer and an aqueous solution.

5. The method of claim 4 further comprising separating the cream layer from the aqueous solution.

6. The method of claim 5 wherein the water is distilled water.

7. The method of claim 5 the step of diluting comprising adding water in a ratio of 1 part to 7.4 parts volume to volume as compared to the egg yolk material.

8. The method of claim 5 the adjusting of the pH and salt content providing a pH level between 5 and 9.

9. The method of claim 5, the viscosity agent comprising algin.

10. The method of claim 5, the viscosity agent comprising carboxy methylcellulose.

11. The method of claim 5 wherein the step of separating the pH adjusted and mixed egg yolk material and water components occurs at a temperature of at least 50° C.

12. The method of claim 5 wherein egg yolks are obtained from eggs laid by hens fed according to a modified feeding program, the modified feeding program comprising standard feed, the addition of between 0 to 100 lbs of extruded whole fat soybeans per ton of the standard feed.

13. The method according to claim 14, said modified feeding program further comprising 50 lbs of flax seed per ton of standard feed.

14. The method of claim 12 wherein a level of omega-6 fatty acid is maintained in the eggs laid by the hens eating feed under the modified feeding program.

15. The method of claim 14 wherein said modified feeding program elevates the level of omega-3 fatty acid in the eggs laid by the hens eating feed under the modified feeding program.

16. The method of claim 15 wherein the aqueous solution is added to infant formula.

17. The method of claim 12 wherein said modified feeding program elevates the level of omega-3 fatty acid while maintaining the level of the omega-6 fatty acid, in the eggs laid by the hens eating feed under the modified feeding program.

18. The method of claim 12 wherein said modified feeding program elevates the level of omega-3 fatty acid to achieve omega-6 fatty acid: omega-3 fatty acid ratios of 4 to 2.4 in the eggs laid by the hens eating feed under the modified feeding program.

19. The method of claim 13 wherein said modified feeding program elevates the level of omega-3 fatty acid, in eggs laid by the hens eating feed under the modified feeding program.

20. The method of claim 13 wherein said modified feeding program elevates the level of omega-3 fatty acid to achieve omega-6 fatty acid: omega-3 fatty acid ratio of 2.1 to 1.9 in the eggs laid by the hens eating feed under the modified feeding program.

* * * * *

UNITED STATES PATENT AND TRADEMARK OFFICE
CERTIFICATE OF CORRECTION

PATENT NO.    : 6,217,926 B1
DATED         : April 17, 2001
INVENTOR(S)   : Jonathan A. Merkle Page 1 of 1

It is certified that error appears in the above-identified patent and that said Letters Patent is hereby corrected as shown below:

Title page
Item [75], delete "Herschell" and insert -- Hershell --;
Item [56], under OTHER PUBLICATIONS, line 2, delete "fo" and insert -- of --;

Column 5,
Line 7, delete "acqueous" and insert -- aqueous --;

Column 8,
Line 11, delete "100°" and insert -- 100° C --;

Column 12,
Line 63, delete "minutes," and insert -- minutes. --;

Signed and Sealed this

Fifth Day of March, 2002

Attest:

Attesting Officer

JAMES E. ROGAN
Director of the United States Patent and Trademark Office